United States Patent
Ma et al.

(10) Patent No.: US 9,730,983 B2
(45) Date of Patent: Aug. 15, 2017

(54) METHODS FOR TREATMENT OF CD14-MEDIATED DISORDERS AND RESPONSES

(71) Applicants: Chih-Yuan Ma, Tainan (TW); Guey-Yueh Shi, Tainan (TW); Hua-Lin Wu, Tainan (TW)

(72) Inventors: Chih-Yuan Ma, Tainan (TW); Guey-Yueh Shi, Tainan (TW); Hua-Lin Wu, Tainan (TW)

( * ) Notice: Subject to any disclaimer, the term of this patent is extended or adjusted under 35 U.S.C. 154(b) by 0 days.

(21) Appl. No.: 14/873,880

(22) Filed: Oct. 2, 2015

(65) Prior Publication Data
US 2017/0095537 A1    Apr. 6, 2017

(51) Int. Cl.
*A61K 38/36*    (2006.01)
*A61K 9/00*    (2006.01)

(52) U.S. Cl.
CPC .......... *A61K 38/366* (2013.01); *A61K 9/0019* (2013.01)

(58) Field of Classification Search
None
See application file for complete search history.

(56) References Cited

U.S. PATENT DOCUMENTS

| | | | | |
|---|---|---|---|---|
| 8,252,905 B2* | 8/2012 | Furusako | .......... | A61K 39/39541 530/387.3 |
| 8,772,239 B2* | 7/2014 | Tsuruta | .................. | A61K 38/00 514/1.4 |
| 2006/0165686 A1* | 7/2006 | Elson | ..................... | C07K 16/18 424/143.1 |

OTHER PUBLICATIONS

Wei et al., Cardiovascular Research, 92, 317-327, 2011.*
Chih-Yuan Ma, Wei-En Chang, Guey-Yueh Shi, Bi-Ying Chang, Sheng-En Cheng, Yun-Tai Shih, and Hua-Lin Wu "Recombinant Thrombomodulin Inhibits Lipopolysaccharide-Induced Inflammatory Response by Blocking the Functions of CD14" The Journal of Immunology 194:1905-1915, 2015.

* cited by examiner

*Primary Examiner* — Elly-Gerald Stoica
(74) *Attorney, Agent, or Firm* — Hsiu-Ming Saunders; Intellectual Property Connections, Inc.

(57) ABSTRACT

A method for blocking, inhibiting and/or decreasing cluster of differentiation 14 (CD14) function, CD14-mediated cellular response and/or treating CD14-mediated pathological conditions is disclosed. The method comprises administering to a subject in need thereof a pharmaceutical composition comprising: (a) a therapeutically effective amount of a recombinant protein comprising an amino acid sequence that is at least 80% identical to SEQ ID NO: 1, wherein the recombinant protein does not comprises a lectin-like domain 1 of a human thrombomodulin; and (b) a pharmaceutically acceptable vehicle, carrier, diluent, excipients, and/or salt.

16 Claims, 4 Drawing Sheets

SEQUENCE LISTING

```
<160> NUMBER OF SEQ ID NOS: 10

<210> SEQ ID NO 1
<211> LENGTH: 274
<212> TYPE: PRT
<213> ORGANISM: Homo sapiens

<400> SEQUENCE: 1

Ala Trp Asp Cys Ser Val Glu Asn Gly Gly Cys Glu His Ala Cys Asn
1               5                   10                  15

Ala Ile Pro Gly Ala Pro Arg Cys Gln Cys Pro Ala Gly Ala Ala Leu
            20                  25                  30

Gln Ala Asp Gly Arg Ser Cys Thr Ala Ser Ala Thr Gln Ser Cys Asn
        35                  40                  45

Asp Leu Cys Glu His Phe Cys Val Pro Asn Pro Asp Gln Pro Gly Ser
    50                  55                  60

Tyr Ser Cys Met Cys Glu Thr Gly Tyr Arg Leu Ala Ala Asp Gln His
65                  70                  75                  80
```

```
Arg Cys Glu Asp Val Asp Asp Cys Ile Leu Glu Pro Ser Pro Cys Pro
                85                  90                  95
Gln Arg Cys Val Asn Thr Gln Gly Gly Phe Glu Cys His Cys Tyr Pro
            100                 105                 110
Asn Tyr Asp Leu Val Asp Gly Glu Cys Val Glu Pro Val Asp Pro Cys
            115                 120                 125
Phe Arg Ala Asn Cys Glu Tyr Gln Cys Gln Pro Leu Asn Gln Thr Ser
        130                 135                 140
Tyr Leu Cys Val Cys Ala Glu Gly Phe Ala Pro Ile Pro His Glu Pro
145                 150                 155                 160
His Arg Cys Gln Met Phe Cys Asn Gln Thr Ala Cys Pro Ala Asp Cys
                165                 170                 175
Asp Pro Asn Thr Gln Ala Ser Cys Glu Cys Pro Glu Gly Tyr Ile Leu
            180                 185                 190
Asp Asp Gly Phe Ile Cys Thr Asp Ile Asp Glu Cys Glu Asn Gly Gly
            195                 200                 205
Phe Cys Ser Gly Val Cys His Asn Leu Pro Gly Thr Phe Glu Cys Ile
        210                 215                 220
Cys Gly Pro Asp Ser Ala Leu Ala Arg His Ile Gly Thr Asp Cys Asp
225                 230                 235                 240
Ser Gly Lys Val Asp Gly Gly Asp Ser Gly Ser Gly Glu Pro Pro Pro
                245                 250                 255
Ser Pro Thr Pro Gly Ser Thr Leu Thr Pro Pro Ala Val Gly Leu Val
            260                 265                 270
His Ser

<210> SEQ ID NO 2
<211> LENGTH: 232
<212> TYPE: PRT
<213> ORGANISM: Homo sapiens

<400> SEQUENCE: 2

Ala Thr Gln Ser Cys Asn Asp Leu Cys Glu His Phe Cys Val Pro Asn
1               5                   10                  15
Pro Asp Gln Pro Gly Ser Tyr Ser Cys Met Cys Glu Thr Gly Tyr Arg
            20                  25                  30
Leu Ala Ala Asp Gln His Arg Cys Glu Asp Val Asp Asp Cys Ile Leu
        35                  40                  45
Glu Pro Ser Pro Cys Pro Gln Arg Cys Val Asn Thr Gln Gly Gly Phe
    50                  55                  60
Glu Cys His Cys Tyr Pro Asn Tyr Asp Leu Val Asp Gly Glu Cys Val
65                  70                  75                  80
Glu Pro Val Asp Pro Cys Phe Arg Ala Asn Cys Glu Tyr Gln Cys Gln
                85                  90                  95
Pro Leu Asn Gln Thr Ser Tyr Leu Cys Val Cys Ala Glu Gly Phe Ala
            100                 105                 110
Pro Ile Pro His Glu Pro His Arg Cys Gln Met Phe Cys Asn Gln Thr
        115                 120                 125
Ala Cys Pro Ala Asp Cys Asp Pro Asn Thr Gln Ala Ser Cys Glu Cys
    130                 135                 140
Pro Glu Gly Tyr Ile Leu Asp Asp Gly Phe Ile Cys Thr Asp Ile Asp
145                 150                 155                 160
Glu Cys Glu Asn Gly Gly Phe Cys Ser Gly Val Cys His Asn Leu Pro
                165                 170                 175
```

Gly Thr Phe Glu Cys Ile Cys Gly Pro Asp Ser Ala Leu Ala Arg His
                180                 185                 190

Ile Gly Thr Asp Cys Asp Ser Gly Lys Val Asp Gly Asp Ser Gly
        195                 200                 205

Ser Gly Glu Pro Pro Ser Pro Thr Pro Gly Ser Thr Leu Thr Pro
    210                 215                 220

Pro Ala Val Gly Leu Val His Ser
225             230

<210> SEQ ID NO 3
<211> LENGTH: 191
<212> TYPE: PRT
<213> ORGANISM: Homo sapiens

<400> SEQUENCE: 3

Asp Val Asp Asp Cys Ile Leu Glu Pro Ser Pro Cys Pro Gln Arg Cys
1               5                   10                  15

Val Asn Thr Gln Gly Gly Phe Glu Cys His Cys Tyr Pro Asn Tyr Asp
            20                  25                  30

Leu Val Asp Gly Glu Cys Val Glu Pro Val Asp Pro Cys Phe Arg Ala
        35                  40                  45

Asn Cys Glu Tyr Gln Cys Gln Pro Leu Asn Gln Thr Ser Tyr Leu Cys
    50                  55                  60

Val Cys Ala Glu Gly Phe Ala Pro Ile Pro His Glu Pro His Arg Cys
65                  70                  75                  80

Gln Met Phe Cys Asn Gln Thr Ala Cys Pro Ala Asp Cys Asp Pro Asn
                85                  90                  95

Thr Gln Ala Ser Cys Glu Cys Pro Glu Gly Tyr Ile Leu Asp Asp Gly
            100                 105                 110

Phe Ile Cys Thr Asp Ile Asp Glu Cys Glu Asn Gly Gly Phe Cys Ser
        115                 120                 125

Gly Val Cys His Asn Leu Pro Gly Thr Phe Glu Cys Ile Cys Gly Pro
    130                 135                 140

Asp Ser Ala Leu Ala Arg His Ile Gly Thr Asp Cys Asp Ser Gly Lys
145                 150                 155                 160

Val Asp Gly Gly Asp Ser Gly Ser Gly Glu Pro Pro Ser Pro Thr
                165                 170                 175

Pro Gly Ser Thr Leu Thr Pro Pro Ala Val Gly Leu Val His Ser
            180                 185                 190

<210> SEQ ID NO 4
<211> LENGTH: 151
<212> TYPE: PRT
<213> ORGANISM: Homo sapiens

<400> SEQUENCE: 4

Pro Val Asp Pro Cys Phe Arg Ala Asn Cys Glu Tyr Gln Cys Gln Pro
1               5                   10                  15

Leu Asn Gln Thr Ser Tyr Leu Cys Val Cys Ala Glu Gly Phe Ala Pro
            20                  25                  30

Ile Pro His Glu Pro His Arg Cys Gln Met Phe Cys Asn Gln Thr Ala
        35                  40                  45

Cys Pro Ala Asp Cys Asp Pro Asn Thr Gln Ala Ser Cys Glu Cys Pro
    50                  55                  60

Glu Gly Tyr Ile Leu Asp Asp Gly Phe Ile Cys Thr Asp Ile Asp Glu
65                  70                  75                  80

Cys Glu Asn Gly Gly Phe Cys Ser Gly Val Cys His Asn Leu Pro Gly
                85                  90                  95

Thr Phe Glu Cys Ile Cys Gly Pro Asp Ser Ala Leu Ala Arg His Ile
            100                 105                 110

Gly Thr Asp Cys Asp Ser Gly Lys Val Asp Gly Gly Asp Ser Gly Ser
            115                 120                 125

Gly Glu Pro Pro Pro Ser Pro Thr Pro Gly Ser Thr Leu Thr Pro Pro
130                 135                 140

Ala Val Gly Leu Val His Ser
145                 150

<210> SEQ ID NO 5
<211> LENGTH: 112
<212> TYPE: PRT
<213> ORGANISM: Homo sapiens

<400> SEQUENCE: 5

Cys Gln Met Phe Cys Asn Gln Thr Ala Cys Pro Ala Asp Cys Asp Pro
1               5                   10                  15

Asn Thr Gln Ala Ser Cys Glu Cys Pro Glu Gly Tyr Ile Leu Asp Asp
            20                  25                  30

Gly Phe Ile Cys Thr Asp Ile Asp Glu Cys Glu Asn Gly Gly Phe Cys
            35                  40                  45

Ser Gly Val Cys His Asn Leu Pro Gly Thr Phe Glu Cys Ile Cys Gly
        50                  55                  60

Pro Asp Ser Ala Leu Ala Arg His Ile Gly Thr Asp Cys Asp Ser Gly
65                  70                  75                  80

Lys Val Asp Gly Gly Asp Ser Gly Ser Gly Glu Pro Pro Pro Ser Pro
                85                  90                  95

Thr Pro Gly Ser Thr Leu Thr Pro Pro Ala Val Gly Leu Val His Ser
            100                 105                 110

<210> SEQ ID NO 6
<211> LENGTH: 75
<212> TYPE: PRT
<213> ORGANISM: Homo sapiens

<400> SEQUENCE: 6

Asp Ile Asp Glu Cys Glu Asn Gly Gly Phe Cys Ser Gly Val Cys His
1               5                   10                  15

Asn Leu Pro Gly Thr Phe Glu Cys Ile Cys Gly Pro Asp Ser Ala Leu
            20                  25                  30

Ala Arg His Ile Gly Thr Asp Cys Asp Ser Gly Lys Val Asp Gly Gly
            35                  40                  45

Asp Ser Gly Ser Gly Glu Pro Pro Pro Ser Pro Thr Pro Gly Ser Thr
        50                  55                  60

Leu Thr Pro Pro Ala Val Gly Leu Val His Ser
65                  70                  75

<210> SEQ ID NO 7
<211> LENGTH: 239
<212> TYPE: PRT
<213> ORGANISM: Homo sapiens

```
<400> SEQUENCE: 7

Ala Trp Asp Cys Ser Val Glu Asn Gly Gly Cys Glu His Ala Cys Asn
1               5                   10                  15

Ala Ile Pro Gly Ala Pro Arg Cys Gln Cys Pro Ala Gly Ala Ala Leu
            20                  25                  30

Gln Ala Asp Gly Arg Ser Cys Thr Ala Ser Ala Thr Gln Ser Cys Asn
        35                  40                  45

Asp Leu Cys Glu His Phe Cys Val Pro Asn Pro Asp Gln Pro Gly Ser
    50                  55                  60

Tyr Ser Cys Met Cys Glu Thr Gly Tyr Arg Leu Ala Ala Asp Gln His
65                  70                  75                  80

Arg Cys Glu Asp Val Asp Asp Cys Ile Leu Glu Pro Ser Pro Cys Pro
                85                  90                  95

Gln Arg Cys Val Asn Thr Gln Gly Gly Phe Glu Cys His Cys Tyr Pro
            100                 105                 110

Asn Tyr Asp Leu Val Asp Gly Glu Cys Val Glu Pro Val Asp Pro Cys
        115                 120                 125

Phe Arg Ala Asn Cys Glu Tyr Gln Cys Gln Pro Leu Asn Gln Thr Ser
    130                 135                 140

Tyr Leu Cys Val Cys Ala Glu Gly Phe Ala Pro Ile Pro His Glu Pro
145                 150                 155                 160

His Arg Cys Gln Met Phe Cys Asn Gln Thr Ala Cys Pro Ala Asp Cys
                165                 170                 175

Asp Pro Asn Thr Gln Ala Ser Cys Glu Cys Pro Glu Gly Tyr Ile Leu
            180                 185                 190

Asp Asp Gly Phe Ile Cys Thr Asp Ile Asp Glu Cys Glu Asn Gly Gly
        195                 200                 205

Phe Cys Ser Gly Val Cys His Asn Leu Pro Gly Thr Phe Glu Cys Ile
    210                 215                 220

Cys Gly Pro Asp Ser Ala Leu Ala Arg His Ile Gly Thr Asp Cys
225                 230                 235

<210> SEQ ID NO 8
<211> LENGTH: 274
<212> TYPE: PRT
<213> ORGANISM: Homo sapiens

<400> SEQUENCE: 8

Ala Trp Asp Cys Ser Val Glu Asn Gly Gly Cys Glu His Ala Cys Asn
1               5                   10                  15

Ala Ile Pro Gly Ala Pro Arg Cys Gln Cys Pro Ala Gly Ala Ala Leu
            20                  25                  30

Gln Ala Asp Gly Arg Ser Cys Thr Ala Ser Ala Thr Gln Ser Cys Asn
        35                  40                  45

Asp Leu Cys Glu His Phe Cys Val Pro Asn Pro Asp Gln Pro Gly Ser
    50                  55                  60

Tyr Ser Cys Met Cys Glu Thr Gly Tyr Arg Leu Ala Ala Asp Gln His
65                  70                  75                  80

Arg Cys Glu Asp Val Asp Asp Cys Ile Leu Glu Pro Ser Pro Cys Pro
                85                  90                  95

Gln Arg Cys Val Asn Thr Gln Gly Gly Phe Glu Cys His Cys Tyr Pro
            100                 105                 110

Asn Tyr Asp Leu Val Asp Gly Glu Cys Val Glu Pro Val Asp Pro Cys
        115                 120                 125
```

```
Phe Arg Ala Asn Cys Glu Tyr Gln Cys Gln Pro Leu Asn Gln Thr Ser
    130                 135                 140

Tyr Leu Cys Val Cys Ala Glu Gly Phe Ala Pro Ile Pro His Glu Pro
145                 150                 155                 160

His Arg Cys Gln Met Phe Cys Asn Gln Thr Ala Cys Pro Ala Asp Cys
                165                 170                 175

Asp Pro Asn Thr Gln Ala Ser Cys Glu Cys Pro Glu Gly Tyr Ile Leu
            180                 185                 190

Asp Asp Gly Phe Ile Cys Thr Asp Ala Asp Glu Cys Glu Asn Gly Gly
        195                 200                 205

Phe Cys Ser Gly Val Cys His Asn Leu Pro Gly Thr Phe Glu Cys Ile
210                 215                 220

Cys Gly Pro Asp Ser Ala Leu Ala Arg His Ile Gly Thr Asp Cys Asp
225                 230                 235                 240

Ser Gly Lys Val Asp Gly Asp Ser Gly Ser Gly Glu Pro Pro Pro
            245                 250                 255

Ser Pro Thr Pro Gly Ser Thr Leu Thr Pro Pro Ala Val Gly Leu Val
            260                 265                 270

His Ser

<210> SEQ ID NO 9
<211> LENGTH: 575
<212> TYPE: PRT
<213> ORGANISM: Homo sapiens

<400> SEQUENCE: 9

Met Leu Gly Val Leu Val Leu Gly Ala Leu Ala Leu Ala Gly Leu Gly
1               5                   10                  15

Phe Pro Ala Pro Ala Glu Pro Gln Pro Gly Gly Ser Gln Cys Val Glu
            20                  25                  30

His Asp Cys Phe Ala Leu Tyr Pro Gly Pro Ala Thr Phe Leu Asn Ala
        35                  40                  45

Ser Gln Ile Cys Asp Gly Leu Arg Gly His Leu Met Thr Val Arg Ser
    50                  55                  60

Ser Val Ala Ala Asp Val Ile Ser Leu Leu Leu Asn Gly Asp Gly Gly
65                  70                  75                  80

Val Gly Arg Arg Arg Leu Trp Ile Gly Leu Gln Leu Pro Pro Gly Cys
                85                  90                  95

Gly Asp Pro Lys Arg Leu Gly Pro Leu Arg Gly Phe Gln Trp Val Thr
            100                 105                 110

Gly Asp Asn Asn Thr Ser Tyr Ser Arg Trp Ala Arg Leu Asp Leu Asn
        115                 120                 125

Gly Ala Pro Leu Cys Gly Pro Leu Cys Val Ala Val Ser Ala Ala Glu
    130                 135                 140

Ala Thr Val Pro Ser Glu Pro Ile Trp Glu Glu Gln Gln Cys Glu Val
145                 150                 155                 160

Lys Ala Asp Gly Phe Leu Cys Glu Phe His Phe Pro Ala Thr Cys Arg
                165                 170                 175

Pro Leu Ala Val Glu Pro Gly Ala Ala Ala Ala Val Ser Ile Thr
            180                 185                 190

Tyr Gly Thr Pro Phe Ala Ala Arg Gly Ala Asp Phe Gln Ala Leu Pro
        195                 200                 205

Val Gly Ser Ser Ala Ala Val Ala Pro Leu Gly Leu Gln Leu Met Cys
    210                 215                 220
```

```
Thr Ala Pro Pro Gly Ala Val Gln Gly His Trp Ala Arg Glu Ala Pro
225                 230                 235                 240

Gly Ala Trp Asp Cys Ser Val Glu Asn Gly Gly Cys Glu His Ala Cys
            245                 250                 255

Asn Ala Ile Pro Gly Ala Pro Arg Cys Gln Cys Pro Ala Gly Ala Ala
            260                 265                 270

Leu Gln Ala Asp Gly Arg Ser Cys Thr Ala Ser Ala Thr Gln Ser Cys
            275                 280                 285

Asn Asp Leu Cys Glu His Phe Cys Val Pro Asn Pro Asp Gln Pro Gly
290                 295                 300

Ser Tyr Ser Cys Met Cys Glu Thr Gly Tyr Arg Leu Ala Ala Asp Gln
305                 310                 315                 320

His Arg Cys Glu Asp Val Asp Asp Cys Ile Leu Glu Pro Ser Pro Cys
            325                 330                 335

Pro Gln Arg Cys Val Asn Thr Gln Gly Gly Phe Glu Cys His Cys Tyr
            340                 345                 350

Pro Asn Tyr Asp Leu Val Asp Gly Glu Cys Val Glu Pro Val Asp Pro
            355                 360                 365

Cys Phe Arg Ala Asn Cys Glu Tyr Gln Cys Gln Pro Leu Asn Gln Thr
370                 375                 380

Ser Tyr Leu Cys Val Cys Ala Glu Gly Phe Ala Pro Ile Pro His Glu
385                 390                 395                 400

Pro His Arg Cys Gln Met Phe Cys Asn Gln Thr Ala Cys Pro Ala Asp
            405                 410                 415

Cys Asp Pro Asn Thr Gln Ala Ser Cys Glu Cys Pro Glu Gly Tyr Ile
            420                 425                 430

Leu Asp Asp Gly Phe Ile Cys Thr Asp Ile Asp Glu Cys Glu Asn Gly
            435                 440                 445

Gly Phe Cys Ser Gly Val Cys His Asn Leu Pro Gly Thr Phe Glu Cys
            450                 455                 460

Ile Cys Gly Pro Asp Ser Ala Leu Ala Arg His Ile Gly Thr Asp Cys
465                 470                 475                 480

Asp Ser Gly Lys Val Asp Gly Gly Asp Ser Gly Ser Gly Glu Pro Pro
            485                 490                 495

Pro Ser Pro Thr Pro Gly Ser Thr Leu Thr Pro Pro Ala Val Gly Leu
            500                 505                 510

Val His Ser Gly Leu Leu Ile Gly Ile Ser Ile Ala Ser Leu Cys Leu
            515                 520                 525

Val Val Ala Leu Leu Ala Leu Leu Cys His Leu Arg Lys Lys Gln Gly
530                 535                 540

Ala Ala Arg Ala Lys Met Glu Tyr Lys Cys Ala Ala Pro Ser Lys Glu
545                 550                 555                 560

Val Val Leu Gln His Val Arg Thr Glu Arg Thr Pro Gln Arg Leu
            565                 570                 575

<210> SEQ ID NO 10
<211> LENGTH: 375
<212> TYPE: PRT
<213> ORGANISM: Homo sapiens

<400> SEQUENCE: 10

Met Glu Arg Ala Ser Cys Leu Leu Leu Leu Leu Pro Leu Val His
1               5                   10                  15

Val Ser Ala Thr Thr Pro Glu Pro Cys Glu Leu Asp Asp Glu Asp Phe
            20                  25                  30
```

-continued

```
Arg Cys Val Cys Asn Phe Ser Glu Pro Gln Pro Asp Trp Ser Glu Ala
            35                  40                  45
Phe Gln Cys Val Ser Ala Val Glu Val Glu Ile His Ala Gly Gly Leu
    50                  55                  60
Asn Leu Glu Pro Phe Leu Lys Arg Val Asp Ala Asp Ala Asp Pro Arg
65                  70                  75                  80
Gln Tyr Ala Asp Thr Val Lys Ala Leu Arg Val Arg Arg Leu Thr Val
                85                  90                  95
Gly Ala Ala Gln Val Pro Ala Gln Leu Leu Val Gly Ala Leu Arg Val
            100                 105                 110
Leu Ala Tyr Ser Arg Leu Lys Glu Leu Thr Leu Glu Asp Leu Lys Ile
            115                 120                 125
Thr Gly Thr Met Pro Pro Leu Pro Leu Glu Ala Thr Gly Leu Ala Leu
        130                 135                 140
Ser Ser Leu Arg Leu Arg Asn Val Ser Trp Ala Thr Gly Arg Ser Trp
145                 150                 155                 160
Leu Ala Glu Leu Gln Gln Trp Leu Lys Pro Gly Leu Lys Val Leu Ser
                165                 170                 175
Ile Ala Gln Ala His Ser Pro Ala Phe Ser Cys Glu Gln Val Arg Ala
            180                 185                 190
Phe Pro Ala Leu Thr Ser Leu Asp Leu Ser Asp Asn Pro Gly Leu Gly
        195                 200                 205
Glu Arg Gly Leu Met Ala Ala Leu Cys Pro His Lys Phe Pro Ala Ile
        210                 215                 220
Gln Asn Leu Ala Leu Arg Asn Thr Gly Met Glu Thr Pro Thr Gly Val
225                 230                 235                 240
Cys Ala Ala Leu Ala Ala Ala Gly Val Gln Pro His Ser Leu Asp Leu
                245                 250                 255
Ser His Asn Ser Leu Arg Ala Thr Val Asn Pro Ser Ala Pro Arg Cys
            260                 265                 270
Met Trp Ser Ser Ala Leu Asn Ser Leu Asn Leu Ser Phe Ala Gly Leu
        275                 280                 285
Glu Gln Val Pro Lys Gly Leu Pro Ala Lys Leu Arg Val Leu Asp Leu
        290                 295                 300
Ser Cys Asn Arg Leu Asn Arg Ala Pro Gln Pro Asp Glu Leu Pro Glu
305                 310                 315                 320
Val Asp Asn Leu Thr Leu Asp Gly Asn Pro Phe Leu Val Pro Gly Thr
                325                 330                 335
Ala Leu Pro His Glu Gly Ser Met Asn Ser Gly Val Val Pro Ala Cys
            340                 345                 350
Ala Arg Ser Thr Leu Ser Val Gly Val Ser Gly Thr Leu Val Leu Leu
            355                 360                 365
Gln Gly Ala Arg Gly Phe Ala
370                 375
```

METHODS FOR TREATMENT OF CD14-MEDIATED DISORDERS AND RESPONSES

FIELD OF THE INVENTION

The present invention relates generally to CD14-mediated function, and more specifically to methods for blocking, inhibiting and/or decreasing CD14-mediated disorders and responses.

BACKGROUND OF THE INVENTION

Thrombomodulin (TM) was originally identified as an anti-coagulant factor that activates protein C. Recent reports suggest that TM is involved in biological processes including cell-cell adhesion, epithelial-mesenchymal transition, and inflammation in addition to haemostasis. TM comprises a C-type lectin-like domain (domain 1, D1), a domain with six epidermal growth factor (EGF)-like structures (domain 2, D2), as serine/threonine-rich domain (domain 3, D3), a transmembrane domain (domain 4, D4), and a cytoplasmic domain (domain 5, D5). Soluble forms of TM are reported high in the plasma of septic patients. Because TM is a natural anti-coagulant protein, recombinant human soluble TM protein (ART-123) effectively reduces disseminated intravascular coagulation.

Furthermore, recombinant TM lectin-like domain (rTMD1) suppresses lipopolysaccharide (LPS)-induced inflammation by binding directly to LPS and high-mobility group box 1 protein. Although the anti-inflammatory activity or activated protein C (APC) has been demonstrated, the pulmonary immune responses to respiratory pathogens and LPS in mice with strongly reduced protein C activation (TM$^{pro/pro}$ mice) are not different from those in wild-type mice, suggesting that TM can modulate host inflammatory response through a protein C-independent mechanism.

CD14, a glycophosphatidylinositol-anchored membrane protein, is a receptor for LPS. It transfers LPS to the Toll-like receptor (TLR) 4/myeloid differentiation factor-2 complex and elicits downstream signaling pathways, including the mitogen-activated protein kinase, nuclear factor-κB, and interferon regulatory factor 3 pathways, resulting in the production of pro-inflammatory cytokines and type I interferons. Recent studies have reported that CD14 is involved in the activation of TLR2, TLR3, TLR7, and TLR9, since CD14-deficeint macrophages and dendritic cells display reduced inflammatory response to the specific ligands of these TLRs. Soluble forms of CD14 have also been detected in circulating blood and facilitate LPS-induced inflammatory response in endothelial and epithelial cells that do not express the membrane form of CD14. These results suggest that CD14 is a critical pattern-recognition receptor in the innate immunity against a broad spectrum of ligands. Accumulating evidence indicates that CD14 contributes to pathological conditions, including sepsis, liver fibrosis, metabolic syndrome, Alzheimer's disease, and neuropathic pain. Mice with CD14 deficiency are resistant to endotoxin shock and reduce dissemination of Gram-negative bacteria. In an experimental cholestasis model, mice with CD14 deletion display reduced liver fibrosis resulting from a decrease in the production of tumor necrosis factor-α (TNF-α) and transforming growth factor-β. Endotoxemia-initiated obesity and insulin resistance can be attenuated by knocking out CD14 in mice. CD14 knockout mice also exhibit a reduced deposition of β-amyloid plaque in the brain via changes in the brain inflammatory environment. In a neuropathic pain model (spinal nerve L5 transection), knockout of CD14 in mice suppresses mechanical allodynia and thermal hyperalgesia. Increased mechanical hypersensitivity in mice is observed after intrathecal injection of soluble CD14. According to these reports, targeting CD14 may be a potential therapeutic strategy in CD14-related diseases.

SUMMARY OF THE INVENTION

In one aspect, the invention relates to a method for blocking, inhibiting and/or decreasing cluster of differentiation 14 (CD14) function, CD14-mediated cellular response and/or treating (CD14-mediated pathological conditions.

In another aspect, the invention relates to a method for treating sepsis, liver fibrosis, metabolic syndrome. Alzheimer's disease, and/or neuropathic pain associated with CD14-mediated inflammatory conditions in a subject in need thereof.

The method comprises administering to a subject in need thereof a pharmaceutical composition comprising: (a) a therapeutically effective amount of a recombinant protein comprising an amino acid sequence that is at least 80% identical to SEQ ID NO: 1, wherein the recombinant protein does not comprises a lectin-like domain 1 of a human thrombomodulin; and (b) a pharmaceutically acceptable vehicle, carrier, diluent, excipients, and/or salt.

In one embodiment of the invention, the CD14 function and/or CD14-mediated cellular response are at least one selected from the group consisting of TNFα production, IL-6 production, lipopolysaccharide (LPS)-induced inflammation, and Toll-like receptor (TLR) activation.

In another embodiment of the invention, the TLR is at least one receptor selected from the group consisting of TLR2, TLR3, TLR4, TLR7, and TLR9.

In another embodiment of the invention, the recombinant protein exhibits little of no protein C activation activity compared to a wild-type thrombomodulin.

In another embodiment of the invention, the recombinant protein is heat inactivated.

In another embodiment of the invention, the recombinant protein comprises an amino acid sequence that is at least 90% identical to the SEQ ID NO: 1.

In another embodiment of the invention, the recombinant protein comprises (a) a truncated thrombomodulin domain 2, which has at least one out of six epidermal growth factor (EGF)-like structures being deleted; and (b) thrombomodulin domain 3.

In another embodiment of the invention, the truncated thrombomodulin domain 2 has at least two out of six epidermal growth factor (EGF)-like structures being deleted.

In another embodiment of the invention, the truncated thrombomodulin domain 2 has at least three out of six epidermal growth factor (EGF)-like structures being deleted.

In another embodiment of the invention, the truncated thrombomodulin domain 2 has at least four out of six epidermal growth factor (EGF)-like structures being deleted.

In another embodiment of the invention, the truncated thrombomodulin domain 2 has at least five out of six epidermal growth factor (EGF)-like structures being deleted.

In another embodiment of the invention, the recombinant protein comprises the second, third, fourth, fifth and sixth epidermal growth factor (EGF)-like structures of s thrombomodulin domain 2.

In another embodiment of the invention, the recombinant protein comprises an amino acid sequence selected from the group consisting of SEQ ID NOs: 1-6 and 8.

In another embodiment of the invention, the CD14-mediated pathological conditions are at least one selected from the group consisting of sepsis, liver fibrosis, metabolic syndrome, Alzheimer's disease, and neuropathic pain.

In another embodiment of the invention, the subject has an inflammatory response syndrome.

In another embodiment of the invention, the subject has an increased level of soluble CD14 in plasma or serum.

In another embodiment of the invention, the administering step is performed by injection.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIG. 5A shows an picture of a gel of mrTMD23, prTMD23, and prTMD23$^{1442A}$ stained with COUMASSIE® Brilliant Blue. FIG. 5B shows a graph of protein C activation by thrombomodulins.

DETAILED DESCRIPTION OF THE INVENTION

Figure 1A:
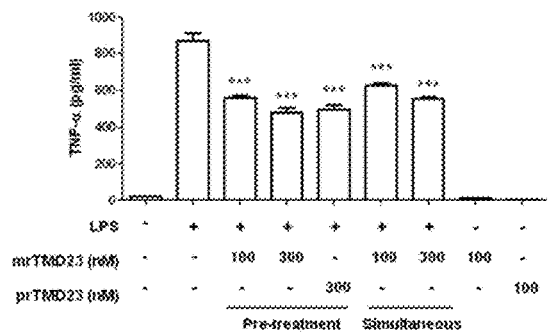
FIGS. 1A-D show that rTMD23 effectively suppresses LPS-induced cytokine production in macrophages through an APC-independent pathway. (A-B) Mouse peritoneal macrophages were incubated with recombinant mammalian-expressed rTMD23 (mrTMD23) or *Pichia*-expressed rTMD23 (prTMD23) for 30 min at 37° C. before LPS (100 ng/ml) stimulation, or simultaneously incubated with mrTMD23 and LPS. After 24 h of LPS stimulation, culture media were harvested for measurement of TNF-α and interleukin-6 (IL-6) concentrations using enzyme-linked immunosorbent assay (ELISA) kits. (C-D) Mouse peritoneal macrophages were incubated with prTMD23 or *Pichia*-expressed recombinant TMD23$^{1442A}$ (prTMD23$^{1442A}$) which cannot activate protein C for 30 min at 37° C. before LPS (100 ng/ml) stimulation. After 24 h of LPS stimulation, culture media were harvested for measurement of TNF-α and IL-6 concentrations using ELISA kits. Data are presented as mean±SEM. *$p<0.05$; $p<0.01$; *$p<0.001$.
Figure 1B:
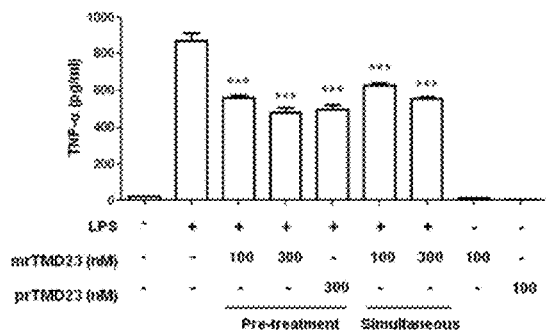

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

Definitions

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The term "treating" or "treatment" refers to administration of an effective amount of a therapeutic agent to a subject in need thereof with the purpose of cure, alleviate, relieve, remedy, ameliorate, or prevent the disease, the symptoms of it, or reduce incidence of symptoms. Such a subject can be identified by a health care professional based on results from any suitable diagnostic method.

"An effective amount" refers to the amount of an active compound that is required to confer a therapeutic effect on the treated subject. Effective doses will vary, as recognized by those skilled in the art, depending on route of administration, excipient usage, and the possibility of co-usage with other therapeutic treatment.

The "Guidance for Industry and Reviewers Estimating the Safe Starting Dose in Clinical Trials for Therapeutics in Adult Healthy Volunteers" published by the U.S. Department of Health and Human Services Food and Drug Administration discloses "a human equivalent dose" may be obtained by calculations from the following formula:

HED=animal dose in mg/kg×(animal weight in kg/human weight in kg)$^{0.33}$.

TEM1 contains the EGF-like domain. The invention relates to the discovery that recombinant TEM1D3 (rTEM1D3) alone functions as an angiogenic factor and promote skin wound healing.

As used herein, when a number or a range is recited, ordinary skill in the art understand it intends to encompass an appropriate, reasonable range for the particular field related to the invention.

By about 0.2-1000 mg it meant that all tenth and integer unit amounts within the range are specifically disclosed as part of the invention. Thus, 0.2, 0.3, 0.4 and 1, 2, 3, 4 . . . 999.7, 999.8, 999.9 and 1000 unit amounts are included as embodiments of this invention.

The length, location relative to the full-length TM precursor, and SEQ ID NOs are shown in Table 1:

TABLE 1

| Protein | Sequence Identifier | LENGTH | ORGANISM | LOCATION |
|---|---|---|---|---|
| TMD23 | SEQ ID NO: 1 | 274 | Homo sapiens | (242) . . . (515) |
| EGF2-6D3 | SEQ ID NO: 2 | 232 | Homo sapiens | (284) . . . (515) |
| EGF3-6D3 | SEQ ID NO: 3 | 191 | Homo sapiens | (325) . . . (515) |
| EGF4-6D3 | SEQ ID NO: 4 | 151 | Homo sapiens | (365) . . . (515) |
| EGF5-6D3 | SEQ ID NO: 5 | 112 | Homo sapiens | (404) . . . (515) |
| EGF6D3 | SEQ ID NO: 6 | 75 | Homo sapiens | (441) . . . (515) |
| TMD2 | SEQ ID NO: 7 | 239 | Homo sapiens | (242) . . . (480) |
| TMD23$^{1442A}$ | SEQ ID NO: 8 | 274 | Homo sapiens | (242) . . . (515) |
| Full-length TM | SEQ ID NO: 9 | 575 | Homo sapiens | (1) . . . (575) |
| CD14 | SEQ ID NO: 10 | 375 | Homo sapiens | (1) . . . (375) |

The terms "rTM," and "rTMD" are interchangeable. The term "rTMD" stands for recombinant thrombomodulin. For example, the amino acid sequence of human rTMD 242 to 515 is listed in SEQ ID NO: 1 (TMD23).

The term mammalian-expressed thrombomodulin, abbreviated "mrTMD", means a recombinant thrombomodulin protein was expressed in a mammalian cell line such as HEK293.

The term Pichia-expressed thrombomodulin, abbreviated "prTMD", means a recombinant protein was expressed in Pichia pastoris, a species of methylotrophic yeast widely used for protein expression.

By "pharmaceutically acceptable" is meant the vehicle, carrier, diluent, excipients, and/or salt must be compatible with the other ingredients of the formulation, and not deleterious to the recipient thereof.

The quantity and nature of the pharmaceutically appropriate vehicle, carrier, diluent, excipients, and/or salt can be easily determined by a person skilled in the art. They are chosen according to the desired pharmaceutical form and method of administration.

Thrombomodulin (TM) is a cell membrane-bound glycoprotein composed of five domains, including a N-terminal lectin-like domain (D1), 6 epidermal growth factor (EGF) repeats (D2), a serine-threonine-rich region (D3), a transmembrane domain (D4) and a short cytoplasmic tail (D5).

The invention relates to the discovery that a recombinant human TM that comprises TM domain 2 plus domain 3 (rTMD23) was able to bind to CD14 and inhibited CD14-mediated inflammatory responses, rTMD23 may be used in the treatment of CD14-related diseases by blocking the functions of CD14. Additionally, a mutant TMD23 which lacks protein C activation was able to block inflammatory responses.

Abbreviations: Thrombomodulin (TM); recombinant TM domain 2 plus domain 3 (rTMD23); lipopolysaccharide (LPS); activated protein C (APC); recombinant mammalian-expressed rTMD23 (mrTMD23); Pichia-expressed rTMD23 (prTMD23).

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Methods and Materials

Preparation of Recombinant Human TM Domains

Methods for the preparation of the TM domains have been described previously (Shi et al., 2005; Shi et al., 2008; Lai et al., 2013). Briefly, pPICZα-A and pCR3-EK vectors (Invitrogen) were used to express and secrete recombinant TM domains from *Pichia pastoris* and human embryonic kidney 293 mammalian protein expression systems. The amino acid contents of TM domains are as follows: rTMD23 ($Ala^{242}$-$Ser^{515}$), recombinant TM EGF-like structure (rT-MEGF) 2-6 and domain 3 (rTMEGF2-6D3) ($Ala^{284}$-$Ser^{515}$), rTMEGF3-6D3 ($Asp^{325}$-$Ser^{515}$), rTMEGF4-6D3 ($Pro^{365}$-$Ser^{515}$), rTMEGF5-6D3 ($Cys^{404}$-$Ser^{515}$), rTMEGF6D3 ($Asp^{441}$-$Ser^{515}$), and rTMD2 ($Ala^{242}$-$Cys^{480}$). To prepare mutant rTMD23, which cannot activate protein C, we mutated the thrombin-binding site (1442A; $rTMD23^{1442A}$) using a QuikChange Site-Directed Mutagenesis Kit (Stratagene).

Cytokine Measurement

C57BL/6 mice (8-12 weeks old) were i.p. injected with 4% thioglycollate. After 4 days, peritoneal macrophages were obtained from the mice as previously described (Ma et al., 2012). For stimulating the mouse peritoneal macrophages, prTMD23 or mrTMD23 was incubated with macrophages for 30 min at 37° C. before LPS (*Escherichia coli*, O111:B4; Sigma-Aldrich) stimulation. prTMD23 and mrTMD23 were heat-inactivated in the presence of 2-mercaptoethanol. Similar procedures were conducted using $prTMD23^{1442A}$, mammalian-expressed recombinant TMEGF2-6D3 (mrTMEGF2-6D3), TMEGF3-6D3 (mrT-MEGF3-6D3), TMEGF4-6D3 (mrTMEGF4-6D3), TMEGF5-6D3 (mrTMEGF5-6D3), TMEGF6D3 (mrTMEGF6D3), and TMD2 (mrTMD2). After 24 h of LPS stimulation, culture media were harvested, and mouse TNF-α and IL-6 levels were determined using ELISA kits (R&D Systems). In some experiments, mrTMD23 and LPS were simultaneously incubated with macrophages for 24 h at 37° C. For the stimulation of HUVECs (Invitrogen), rCD14 (R&D Systems) was incubated with prTMD23 or $prTMD23^{1442A}$ for 30 min at 37° C. LPS, CpO-ODN (InvivoGen), rCD14/prTMD23, and rCD14/$prTMD23^{1442A}$ were incubated with HUVECs for 24 h at 37° C. Culture media were harvested for measurement of IL-6 levels using an ELISA kit (R&D Systems).

Solid Phase Binding Assay and Surface Plasmon Resonance Analysis rCD14 was incubated with prTMD23 or $prTMD23^{1442A}$ containing 0.5% bovine serum albumin/0.05% Tween-20/PBS for 30 min at 37° C. The mixtures were added to wells immobilized with mouse anti-human CD14 antibody (R&D Systems). Recombinant proteins were identified using biotinylated rabbit anti-c-Myc antibody (Cell Signaling Technology). The absorbance was analyzed at 450 nm after incubation with horseradish peroxidase-conjugated streptavidin and substrate development. For performing SPR analysis, mrTMD23 (10 µM) was diluted in HBS-P buffer (0.01 M HEPES, 0.15 M NaCl, 0.005% Surfactant P20; pH; 7.4) and immobilized on NTA sensor chips. rCD14 (R&D Systems) diluted in HBS-P buffer (GE Healthcare) was passed over the immobilized NTA chips. NTA sensor chips and reagent kits were purchased from GE Healthcare, and analysis was performed by BIAcore 3000 instrument (GE Healthcare). The $K_D$ value was evaluated with BIAevaluation software (GE Healthcare).

Endotoxemia Model

To observe the effect of recombinant TM domains on endotoxemia, C57BL/6 mice were i.p. injected with prTMD23 or $prTMD23^{1442A}$. After 30 min, they were i.p. injected with LPS (20 mg/kg; *E. coli*, O111:B4, Sigma-Aldrich). All animal experiments were approved by The Institutional Animal Care and Use Committee of National Cheng Kung University.

Statistical Analyses

Statistical significance was analyzed using one-way ANOVA with a Bonferroni post-test and parametric unpaired t test. Differences between more than two groups were compared using two-way ANOVA with a Bonferroni post-test. Survival data were analyzed using a log-rank test. The p values <0.05 were considered statistically significant.

Figure 1C:
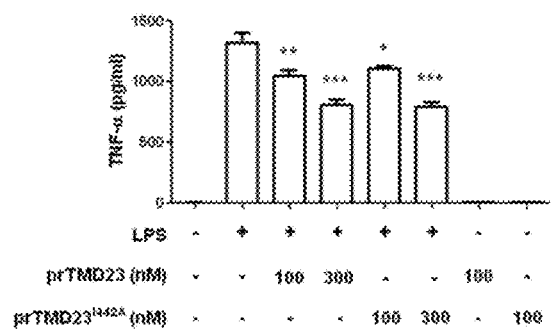
Figure 1D:
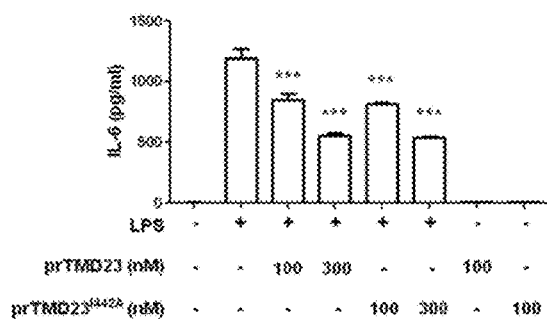

Example 1 rTMD23 Effectively Suppresses LPS-Induced Inflammatory Cytokine Production in Macrophages Through an APC-Independent Pathway We demonstrated that both prTMD23 and mrTMD23 significantly suppressed TNF-α and IL-6 production in macrophages after LPS stimulation (FIGS. 1A, B). These data suggest that rTMD23 inhibits LPS-induced inflammation, and that mammalian- and *Pichia*-expressed rTMD23 similarly suppress LPS-induced inflammation. In addition, prTMD23 and $prTMD23^{1442A}$ showed a similar activity in the inhibition of LPS-induced inflammatory cytokine secretion by macrophages (FIGS. 1C, D). These data suggest that the anti-inflammatory activity of rTMD23 is independent of the APC pathway.

Example 2 rTMD23 Interacts Directly with CD14 and Inhibits CD14-Mediated Inflammation

Figure 2A:
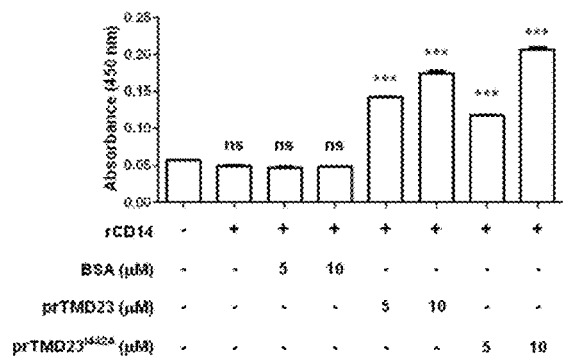
FIGS. 2A-E show that rTMD23 interacts directly with CD14 and inhibits the functions of CD14. (A) recombinant CD14 (rCD14; 100 nM) was incubated with bovine serum albumin, prTMD23, or prTMD23$^{1442A}$ for 30 min at 37° C., and the mixture were incubated in wells immobilized with mouse anti-human CD14 antibody. Biotinylated rabbit anti-c-Myc antibody was used to detect prTMD23 and prTMD23$^{1412A}$. The absorbance was analyzed at 450 nm after incubation with horseradish peroxidase-conjugated streptavidin and 3,3',5,5-tetramethylbenzidine substrate development. (B) Surface plasmon resonance analysis was performed by BIAcore 3000 instrument and $K_D$ value was evaluated with BIAevaluation software. (C-E) rCD14 (100 nM) was pre-incubated with prTMD23 or prTMD23$^{1442A}$ for 30 min at 37° C. and the complexes and LPS (100 ng/ml) or Cytosine-phosphodiester-guanine oligodeoxynueleotide (CpG-ODNs) (10 μg/ml) were incubated with human umbilical vein endothelial cells (HUVECs) for 24 h at 37° C. Culture media were harvested for measurement of IL-6 concentrations using an ELISA kit. prTMD23 or rCD14 was heat-inactivated in the presence of 2-mecaptoethanol. Data are presented as mean±SEM. ***$p<0.001$. ns, no significance.
Figure 2B:
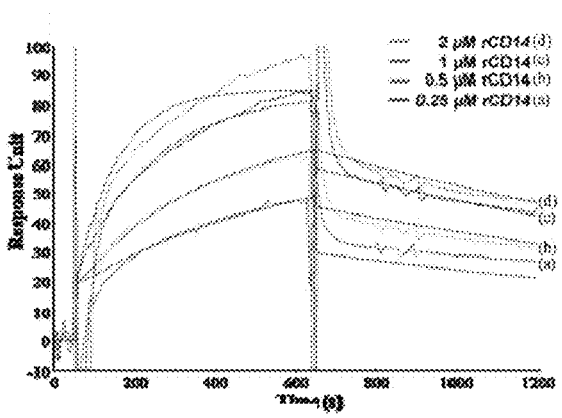
Figure 2C:
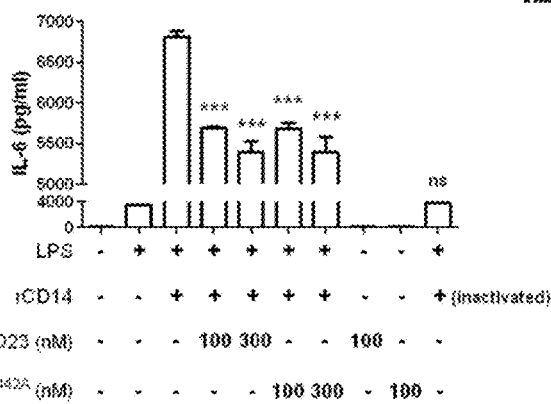
Figure 2D:
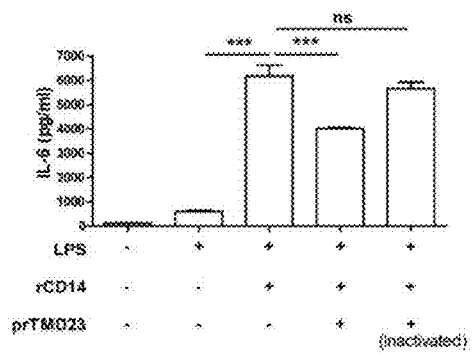
Figure 2E:
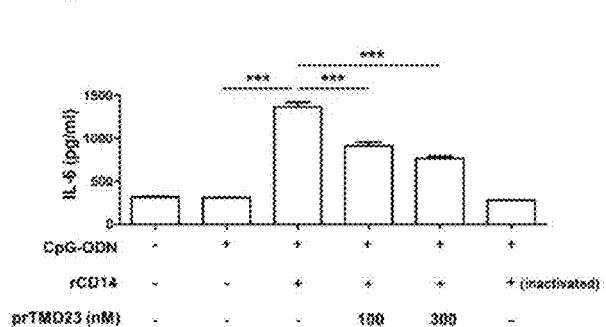

Both prTMD23 and $prTMD23^{1442A}$ interacted directly with rCD14 using solid phase binding assay (FIG. 2A), and SPR analysis showed that the $K_D$ value of the interaction between mrTMD23 and rCD14 was $1.27 \times 10^{-5}$ M (FIG. 2B). To analyze whether rTMD23 specifically inhibits the functions of CD14, we used endothelial cells, which do not express the membrane form of CD14. The results showed that LPS-induced IL-6 secretion by HUVECs was extensively increased in the presence of rCD14; however, heat-inactivated rCD14 did not promote LPS-induced IL-6 production (FIG. 2C). Additionally, treatment with prTMD23 or $prTMD23^{1442A}$ markedly reduced the secretion of IL-6 by HUVECs after stimulation with LPS and rCD14 (FIG. 2C), whereas heat-inactivated prTMD23 did not suppress IL-6 production by HUVECs after stimulation with LPS and rCD14 (FIG. 2D). We also used CpG-ODN, a TLR9 ligand, to stimulate HUVECs. As shown in FIG. 3E, the addition of rCD14 greatly enhanced IL-6 production elicited by CpG-OD, and prTMD23 suppressed CpG-ODN-induced IL-6 secretion by HUVECs.

Figure 3A:
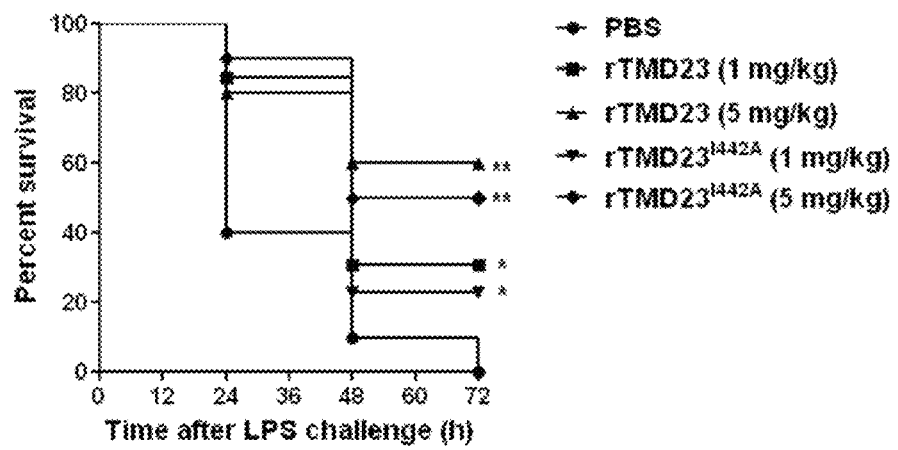
FIGS. 3A-C show that pre-treatment with rTMD23 effectively increases the survival rate and decreases inflammatory response to LPS in mice. (A-C) Phosphate buffered saline (PBS), prTMD23, and prTMD23$^{1442A}$ were intraperitoneally (i.p.) injected into mice. After 30 min, mice were i.p. injected with LPS (20 mg/kg). Mouse survival was monitored every 24 h post-LPS stimulation. n=10-13 mice per each group. Body temperature and serum IL-6 were measured 24 h after LPS stimulation (n=8 mice per each group). Data are presented as mean SEM. *$p<0.05$; $p<0.01$; *$p<0.001$.
Figure 3B:
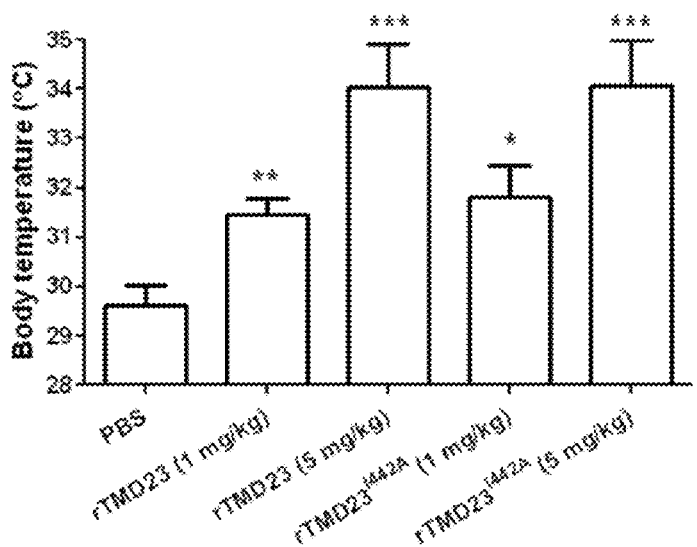
Figure 3C:
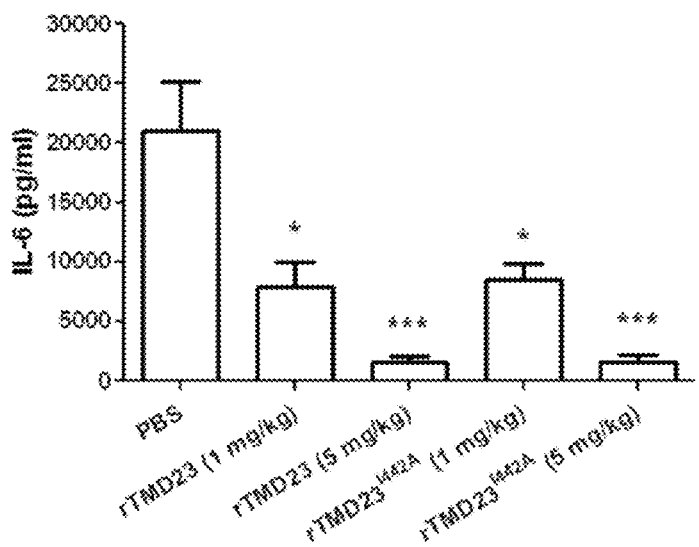

Example 3 rTMD23 Improves Mouse Survival and Reduces Inflammatory Response in Endotoxemia As shown in FIG. 3A, treatment with prTMD23 or prTMD23$^{1442A}$ increased mouse survival after LPS challenge. Consistently higher body temperature and lower serum IL-6 concentrations were observed in mice after treatment with prTMD23 and prTMD23$^{1442A}$ than in those belonging to the PBS group (FIGS. 3B, C).

Example 4

TM D3 Domain is Essential for the Anti-Inflammatory Activity of rTMD23

Figure 4A:
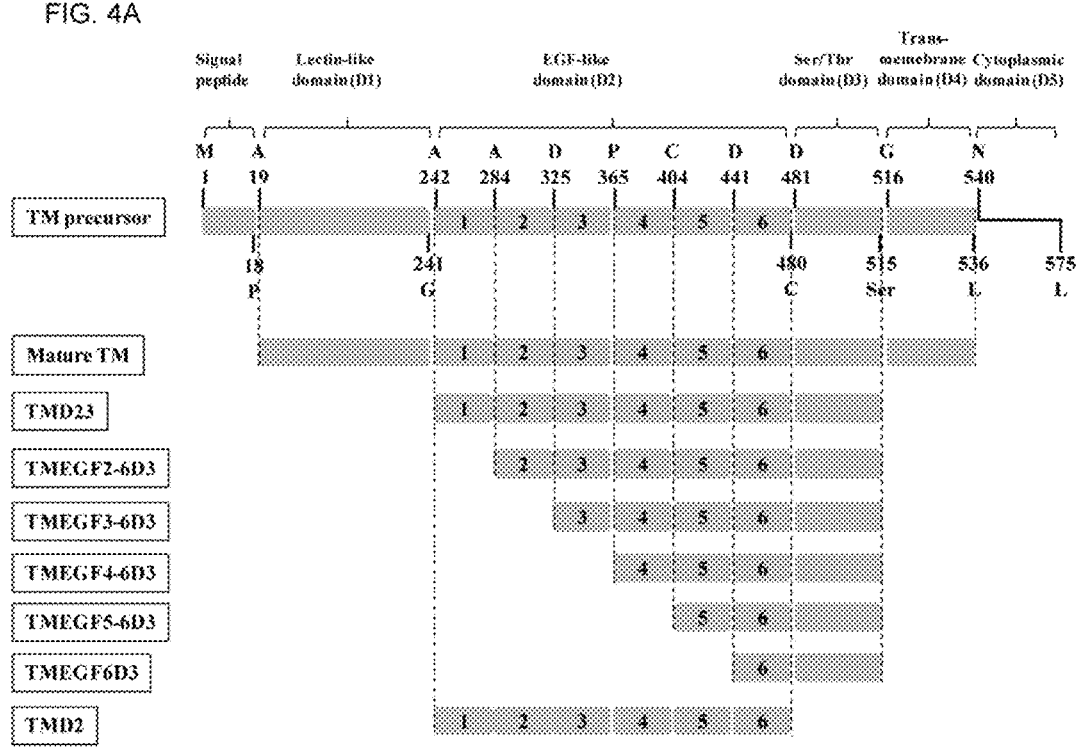
FIGS. 4A-C show that TM D3 domain is required for the anti-inflammatory activity of rTMD23. (A) A cartoon picture of recombinant truncated TM domains. The full-length TM precursor (SEQ ID NO: 9), mature TM, TMD 23 (SEQ ID NO: 1), and various truncated TM domains (SEQ ID NOs: 2-7) are illustrated. (B) Macrophages were treated with recombinant truncated TM domains for 30 min at 37° C. before stimulation with LPS (100 ng/ml). After 24 h of LPS stimulation, the levels of TNF-α were measured by an ELISA kit. (C) Recombinant truncated TM domains were incubated with rCD14 for 30 min at 37° C. and the complexes and LPS (100 ng/ml) were stimulated HUVECs for 24 h at 37° C. The concentrations of IL-6 were determined using an ELISA kit. Data are presented as mean±SEM. *$p<0.05$; $p<0.01$; *$p<0.001$. ns, no significance.
Figure 4B:
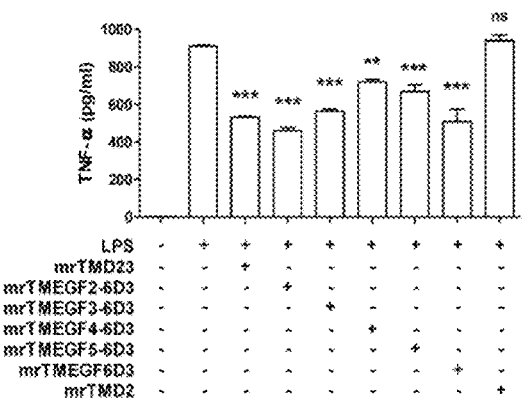
Figure 4C:
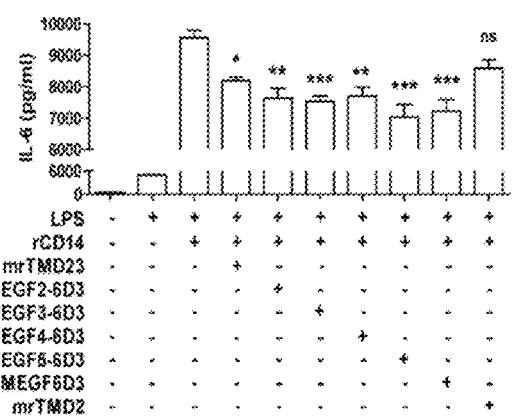

To investigate which domain of rTMD23 is critical for its anti-inflammatory activity, we generated a series of recombinant truncated domains of rTMD23, including mrTMEGF2-6D3, mrTMEGF3-6D3, mrTMEGF4-6D3, mrTMEGF5-6D3, mrTMEGF6D3, and mrTMD2 (FIG. 4A). We found that all of the recombinant truncated domains, except mrTMD2, suppressed LPS-induced inflammation in both macrophages (FIG. 4B) and HUVECs (FIG. 4C). Therefore, TMD3 domain is required for the anti-inflammatory activity of rTMD23.

Example 5

Protein C Activation Prevented by TMD$^{1442A}$ Mutation

Figure 5A:
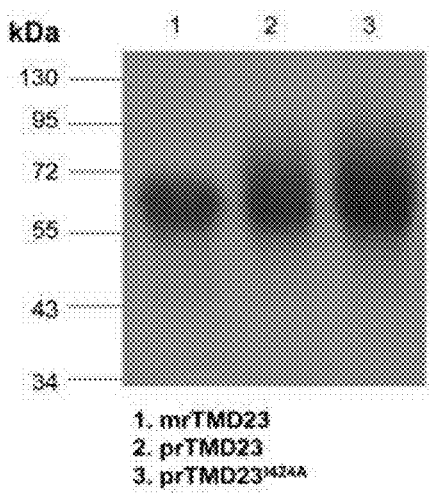
FIGS. 5A-B show protein C activation prevented by TMD$^{1442A}$ mutation.
Figure 5B:
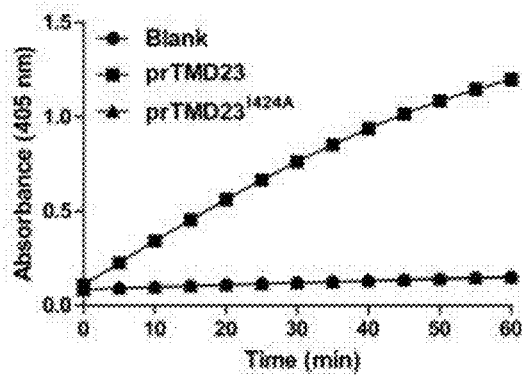

FIG. 5A shows COOMASSIE® Brilliant Blue staining of mrTMD23, prTMD23, and prTMD23$^{1442A}$, indicating equivalent molecular size. In FIG. 5B, prTMD23 (0.4 µg/µl) or prTMD23$^{1442A}$ (0.4 µg/µl) was incubated with thrombin (37.5 nM) and protein C (5 µg/ml) in buffer containing 20 mM Tris (pH 7.4), 0.15 M NaCl, 2.5 mM CaCl$_2$, and 5 mg/mL BSA for 30 min at 37° C. Protein C activation was terminated by adding 40 µl antithrombin III (6 IU/ml) and heparin (12 IU/ml). The enzymatic activity of APC was measured with peptide substrate H-D-Lys(c-Cbo)-Pro-Arg-pNA.2AcOH (SPECTROZYME PCa 1.5 mM) at 37° C. Absorbance was measured at 405 nm. These data show that TMD23 activates Protein C but TMD23$^{1442A}$ does not, indicating that the C protein activation activity of TMD23 is separable from its ability to suppress inflammation.

In summary, it was discovered that recombinant TM domain 2 plus domain 3 (rTMD23) can bind to CD14 and inhibit CD14-mediated inflammatory response. rTMD23 may be used in treatment of CD14-related diseases by blocking the functions of CD14, See Chih-Yuan Ma et al. "Recombinant Thrombomodulin Inhibits Lipopolysaccharide-Induced Inflammatory Response by Blocking the Functions of CD14" *The Journal of Immunology*, 2015, 194: 1905-1915, which is incorporated herein by reference in its entirety.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A method for blocking, inhibiting and/or decreasing cluster of differentiation 14 (CD14) function, CD14-mediated cellular response and/or treating CD14-mediated pathological conditions, comprising:

administering to a subject in need thereof a pharmaceutical composition comprising:

(a) a therapeutically effective amount of a recombinant truncated human thrombomodulin comprising an amino acid sequence selected from the group consisting of SEQ ID NOs: 1 to 6, and 8, wherein the recombinant truncated human thrombomodulin does not comprise domain 1 of human thrombomodulin; and (b) a pharmaceutically acceptable vehicle, carrier, diluent, excipients, and/or salt, wherein the recombinant protein is not heat inactivated, and further wherein the CD14-mediated pathological conditions are at least one selected from the group consisting of sepsis, liver fibrosis, metabolic syndrome, Alzheimer's disease, and neuropathic pain.

2. The method of claim 1, wherein the CD14 function and/or CD14-mediated cellular response are at least one selected from the group consisting of TNFα production, IL-6 production, lipopolysaccharide (LPS)-induced inflammation, and Toll-like receptor (TLR) activation.

3. The method of claim 2, wherein the TLR is at least one receptor selected from the group consisting of TLR2, TLR3, TLR4, TLR7, and TLR9.

4. The method of claim 1, wherein the recombinant protein exhibits little or no protein C activation activity compared to a wild-type thrombomodulin.

5. The method of claim 1, wherein the recombinant protein does not comprise the first epidermal growth factor (EGF)-like structure.

6. The method of claim 1, wherein the recombinant truncated human thrombomodulin does not comprise the first, and second EGF-like structures.

7. The method of claim 1, wherein the recombinant truncated human thrombomodulin does not comprise the first, second, and third EGF-like structures.

8. The method of claim 1, wherein the recombinant truncated human thrombomodulin does not comprise the first, second, third, and fourth EGF-like structures.

9. The method of claim 1, wherein the recombinant truncated human thrombomodulin does not comprise the first, second, third, fourth, and fifth EGF-like structures.

10. The method of claim 1, wherein the recombinant truncated human thrombomodulin comprises the second, third, fourth, fifth and sixth epidermal growth factor (EGF)-like structures of thrombomodulin domain 2.

11. The method of claim 1, wherein the subject has an inflammatory response syndrome.

12. The method of claim 1, wherein the subject has an increased level of soluble CD14 in plasma or serum.

13. The method of claim 1, wherein the administering step is performed by injection.

14. A method for treating sepsis, liver fibrosis, metabolic syndrome, Alzheimer's disease, and/or neuropathic pain associated with CD14-mediated inflammatory conditions in a subject in need thereof, comprising:
administering to the subject a pharmaceutical composition comprising:
(a) a therapeutically effective amount of a recombinant truncated human thrombomodulin comprising an amino acid sequence selected from the group consisting of SEQ ID NOs: 1 to 6, and 8, wherein the recombinant truncated human thrombomodulin does not comprise domain 1 of human thrombomodulin; and
(b) a pharmaceutically acceptable vehicle, carrier, diluent, excipients, and/or salt,
wherein the recombinant protein is not heat inactivated.

15. The method of claim 1, wherein the recombinant protein exhibits little or reduced protein C activation activity compared to a wild-type thrombomodulin.

16. A method for blocking, inhibiting and/or decreasing cluster of differentiation 14 (CD14) function, CD14-mediated cellular response and/or treating CD14-mediated pathological conditions, comprising:
administering to a subject in need thereof a pharmaceutical composition comprising:
(a) a therapeutically effective amount of a recombinant truncated human thrombomodulin comprising an amino acid sequence selected from the group consisting of SEQ ID NOs: 1 to 6, and 8, wherein the recombinant truncated human thrombomodulin does not comprise domain 1 of human thrombomodulin; and
(b) a pharmaceutically acceptable vehicle, carrier, diluent, excipients, and/or salt,
wherein the recombinant protein is not heat inactivated and exhibits little or no protein C activation activity compared to a wild-type thrombomodulin; and
further wherein the CD14-mediated pathological conditions are at least one selected from the group consisting of inflammatory conditions, sepsis, atherosclerosis, liver fibrosis, metabolic syndrome, Alzheimer's disease, and neuropathic pain.

* * * * *